United States Patent [19]

Shek

[11] Patent Number: 5,778,474
[45] Date of Patent: Jul. 14, 1998

[54] MECHANICALLY DRIVEN TOOTHBRUSH

[75] Inventor: Kwok-Nam Shek, Hong Kong, Hong Kong

[73] Assignee: Addway Engineering Limited, Hong Kong, Hong Kong

[21] Appl. No.: 749,112

[22] Filed: Nov. 14, 1996

Related U.S. Application Data

[63] Continuation-in-part of Ser. No. 551,431, Nov. 1, 1995, abandoned.

[51] Int. Cl.$^6$ .............................. A16B 13/02; A16B 7/06
[52] U.S. Cl. .............................................. 15/22.1

[56] References Cited

U.S. PATENT DOCUMENTS

| | | | |
|---|---|---|---|
| 2,175,975 | 10/1939 | Steiner | 15/22.1 |
| 5,077,855 | 1/1992 | Ambasz | 15/22.1 |
| 5,186,627 | 2/1993 | Amit | 15/22.1 |
| 5,259,083 | 11/1993 | Stansbury, Jr. | 15/22.1 |
| 5,504,958 | 4/1996 | Herzog | 15/22.1 |

FOREIGN PATENT DOCUMENTS

| | | | |
|---|---|---|---|
| 0460610 | 12/1991 | European Pat. Off. | 15/22.1 |
| 2247297 | 2/1992 | United Kingdom | 15/22.1 |

*Primary Examiner*—David Scherbel
*Assistant Examiner*—Randall E. Chin
*Attorney, Agent, or Firm*—Miller, Sisson, Chapman & Nash, P.C.

[57] ABSTRACT

A toothbrush has a thin, metal cam shaft rotatably driven about a central longitudinal axis. Tuft blocks are mounted in a head member and constrained to pivot about an axis of a support shaft. Upper sides of the tuft blocks each have a slot which fits somewhat loosely over the cam shaft. During use, the cam shaft causes upstanding ends of bristles to move from side to side.

6 Claims, 4 Drawing Sheets

MECHANICALLY DRIVEN TOOTHBRUSH

This invention is a continuation-in-part application of U.S. Pat. application Ser. No. 08/551.431. filed Nov. 1, 1995, now abandoned. The invention relates to mechanically driven toothbrushes.

BACKGROUND OF THE INVENTION

It has already been proposed in U.S. Pat. No. 5,259,083 and in prior art documents referred to in that Patent, to cause the bristle tufts of a toothbrush to move relative to a toothbrush head member. Such movement is provided by a motor normally supported in a toothbrush handle and driven by batteries or other electrical power supply as preferred. It is necessary to transfer or to convert the rotational motion provided by the motor to the tufts and various mechanisms are disclosed in the prior art up to the present day. In U.S. Pat. No. 5,259,083 the rotational drive of a motor is converted to up and down motion by constraining each tuft holder to slide and by causing the sliding using a rotationally driven cam shaft. The toothbrush described in U.S. Pat. No. 5,259,083 is unable to provide desirable "rocking" or side-to-side movement of ends of the bristles and the particular design has certain mechanical drawbacks that make manufacturing the product parts relatively expensive.

SUMMARY OF THE INVENTION

It is an object of the invention to overcome or at least reduce these problems.

According to the invention, there is provided a power driven mechanical toothbrush having an elongate shank extending to a toothbrush head member for supporting a plurality of tuft blocks. A thin, metal cam shaft is adapted to be rotatably driven at high speeds within the shank, has a central longitudinal axis, and is supported by high speed bearing surfaces. The tuft blocks are pivotally supported by the head member about an axis parallel to and spaced apart from the longitudinal axis of the shaft. The blocks have respective slots that fit loosely over the cams of the cam shaft such that when the cam shaft is rotated, upstanding remote ends of bristle tufts in the tuft blocks move from side to side with respect to the shank.

A plurality of tuft blocks may be held stationary in the head member by either enlarging the slot in the block or using a shortened cam shaft and a bearing insert.

The integral cam shaft has a cam section with a plurality of cams, some of which may be in a first plane and the remainder of which may be in planes separated by 180° from the first plane.

The toothbrush may include a disengageable mechanical coupling between a first end of the cam shaft and an electric motor drive shaft of a high speed electric motor.

BRIEF DESCRIPTION OF THE DRAWINGS

A toothbrush according to the invention will now be described by way of example with reference to the accompanying drawings.

DESCRIPTION OF THE PREFERRED EMBODIMENT

Figure 1:
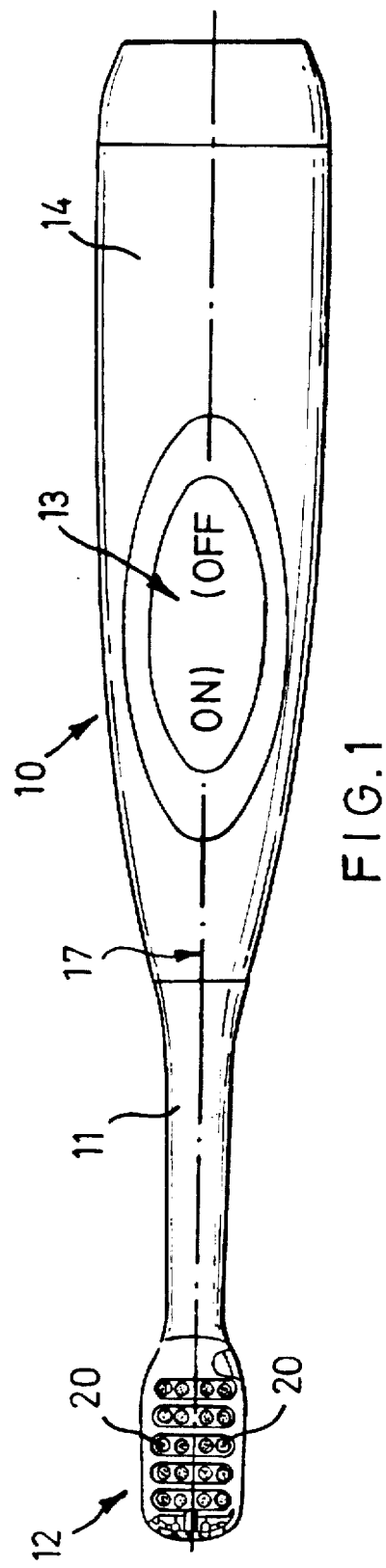
FIG. 1 is a bottom plan view of the toothbrush.
Figure 2:
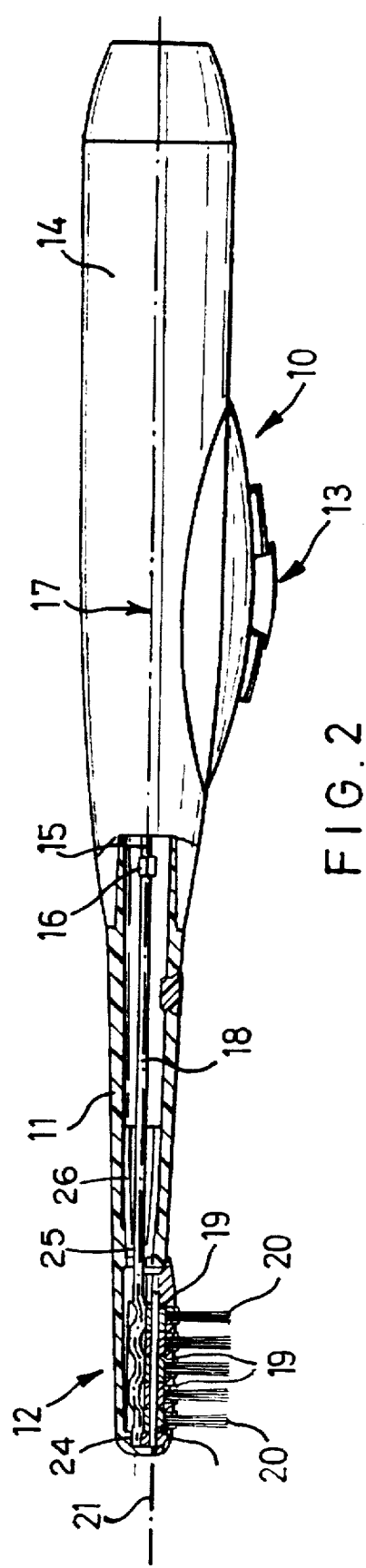
FIG. 2 is a part-sectioned side view of FIG. 1.

Referring to the drawings, in FIGS. 1 and 2 a toothbrush 10 has a shank 11 extending to a toothbrush head member 12. Control switches 13 are provided on an outer surface of a handle 14, and a high speed electric motor and a battery (not shown) are mounted inside the handle 14. The motor operates at speeds of 5500–7500 rpm.

A motor drive shaft 15 extends to a disengageable mechanical coupling 16 connecting the motor to a thin, metal cam shaft 18 that is rotatably mounted in the shank 11 about a longitudinal axis 17. The shaft 18 is constructed of a thin, metal wire having an overall length of approximately 8 cm. The wire diameter is approximately 1.2 mm. The head member 12 pivotally supports five tuft blocks 19, each block having four sets or tufts of bristles 20. The blocks are mounted in the head member 12 and constrained to pivot about an axis 21 which is parallel to and spaced apart from the axis 17.

Figure 3:
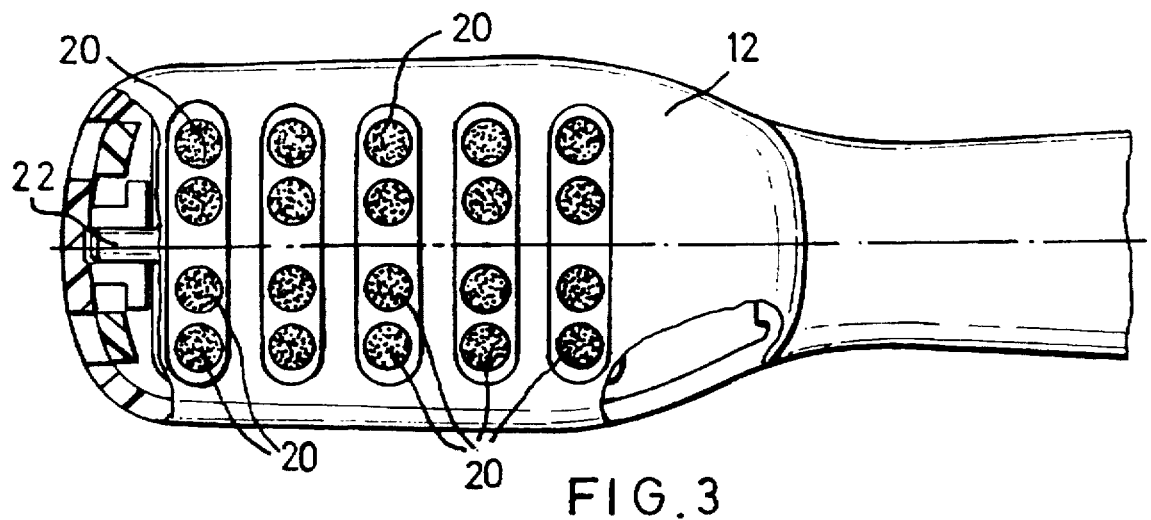
FIG. 3 shows a partly cut-away bottom plan view of a toothbrush head member of the toothbrush.
Figure 4:
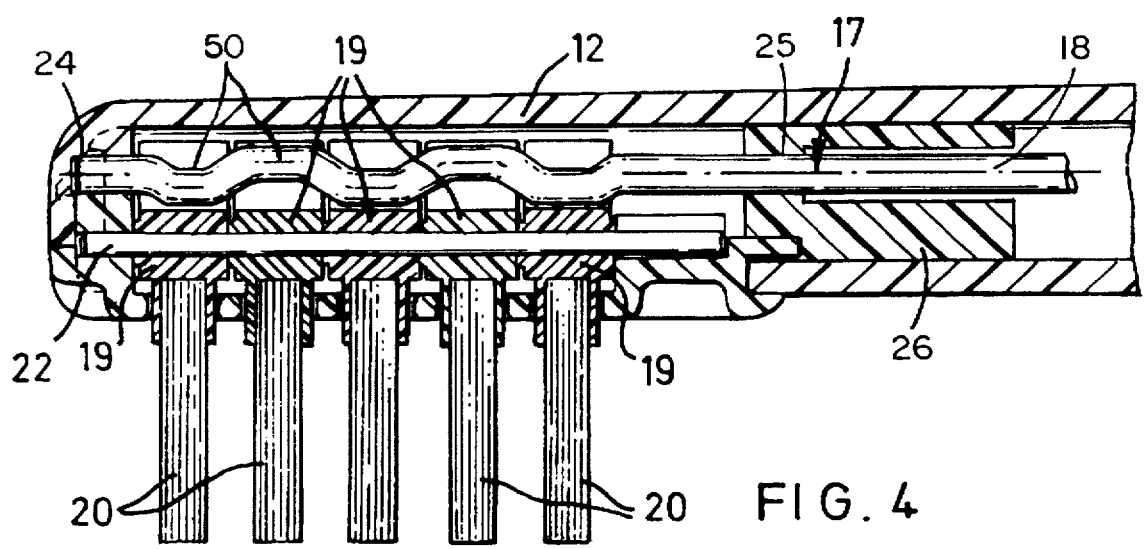
FIG. 4 shows a sectional side view of FIG. 3.

In FIGS. 3 and 4, a shaft 22 provides the pivoting support for all the tuft blocks 19 and has its axis spaced apart from the axis 17 as required. Each tuft block has a slot 23 in its upper surface (see FIG. 5) which is loosely fit over cams 50 of the cam section of the cam shaft 18. It will be noted that the cam section of the cam shaft 18 is constrained along the axis 17 by a bearing 24 at its remote end at one end of the head member 12 and a bearing 25 provided by a replaceable insert 26 supported at the opposite end of the head member 12.

Figure 5:
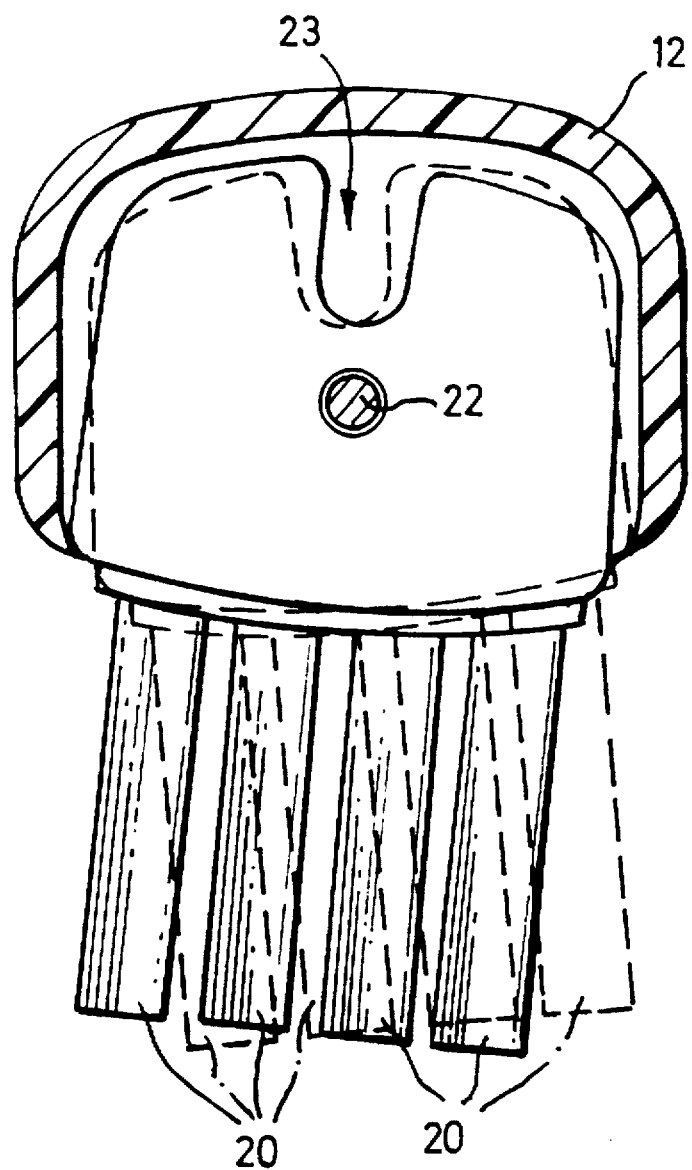
FIG. 5 is a sectioned view of the toothbrush head member to show one tuft block more clearly.

Thus, as the cam shaft 18 is rotated about the axis 17, the cams 50 rotate in the slots 23 and cause the tuft blocks 19 to rock or move about the axis 21. As a result, the remote ends of the bristles in the tufts move from side to side with respect to the shank 11. FIG. 5 shows the extremes of the side to side movement, one extreme being shown in dotted outline.

Bearings 24 and 25 reduce the flexing movement of thin, metal shaft 18 at speeds in the range of 5500 rpm to 7500 rpm, and preferably at approximately 7000 rpm. There must be a minimum of deviation of the shaft 18 and cams 50 from a fixed rotational axis corresponding to axis 17; otherwise, the tuft holders 19 and bristles 20 simply rattle rather than rock from side to side.

It will be appreciated that the shank 11 with its head member 12 may be removed from the handle 14 and replaced by another like shank and member. It will also be appreciated that the pivoting mounting of the tuft blocks is much simpler to provide, more secure and the parts easier to manufacture, than is the case where the tuft holders must slide in the head member, such as disclosed in U.S. Pat. No. 5,259,083.

It will be noted that the planes of the cams 50 are alternatively at angles of 180° to one another. These angles can be different but are preferably arranged so that adjacent cam planes are separated by at least 100° from each adjacent cam plane. Indeed in the more preferred arrangements, the cam is arranged so that directly adjacent, or adjacent movable, tuft blocks move at all times in opposite directions in use.

Preferably all the parts shown in the drawings are formed of plastics materials except the metal, wire, cam shaft 18. Bearings 24 and 25 may be impregnated with graphite lubricant or the like.

Figure 6:
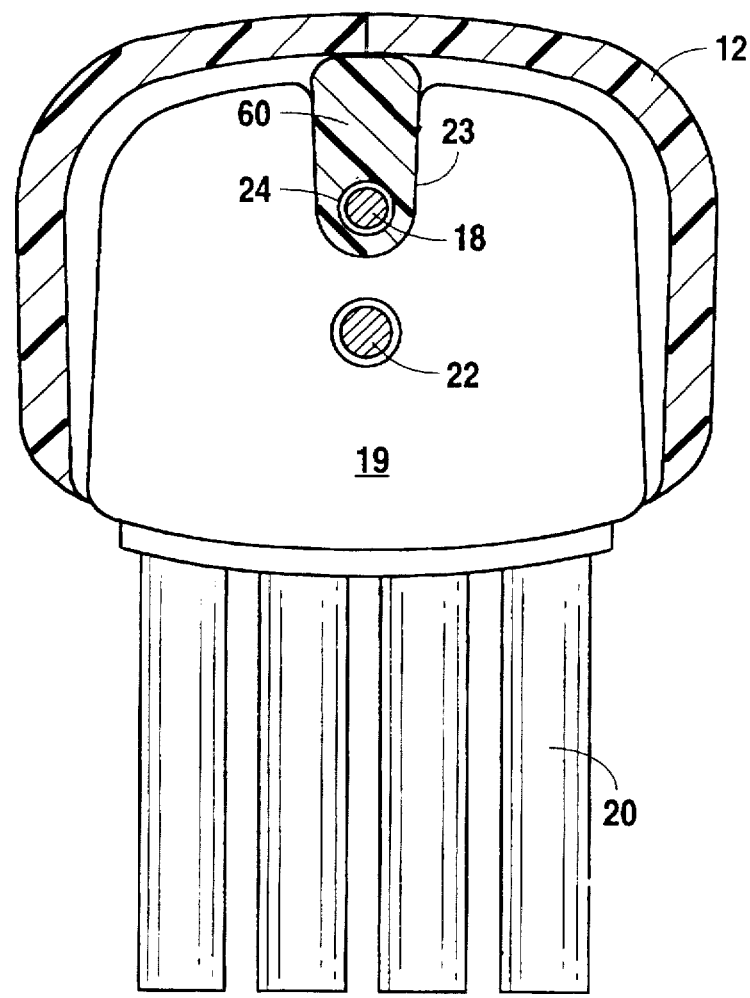
FIG. 6 illustrates a sectioned view of the toothbrush head member showing the bearing insert in a stationary tuft block.

It will be appreciated that in the described embodiment some of the tuft blocks may be held stationary and arranged with larger slots so that the cams 50 of the cam shaft 18 can rotate freely within such a slot. Alternatively, if one or more stationary tuft blocks is adjacent the farthest end from the shank, the cam shaft may be shortened so as to not extend to engage such blocks. In such a case, restraining bearing 24 may be formed by placing a bearing insert 60 in slot 23 to support the end of the shortened cam shaft and restrict the flexing of the shaft at high speeds (see FIG. 6).

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

I claim:

1. A power driven mechanical toothbrush comprising:

an elongate shank;

a toothbrush head member attached to said shank, said head supporting a plurality of tuft blocks, said blocks having bristle tufts therein, said tufts having upstanding remote ends;

a cam shaft rotatably driven at speeds in the range of 5500 rpm to 7500 rpm within said shank, said shaft having a central longitudinal axis, said shaft formed by a wire extending directly from a motor to said head member, said shaft having a cam section that fits inside said head member;

a bearing at each end of said cam section of said shaft to minimize deflection of said cam section from said central longitudinal axis;

said tuft blocks pivotally supported by said head member about an axis parallel to and spaced apart from said central longitudinal axis, said tuft blocks having respective slots that fit loosely over said cam section such that when said cam shaft is rotated, said upstanding remote ends of said bristle tufts in said tuft blocks move from side to side with respect to said shanks; and a bearing insert engaged in one of said slots of one of said blocks, said insert supporting and restricting deflection of said cam section.

2. A toothbrush according to claim 1 wherein at least one of said tuft blocks is held stationary in said head member.

3. A toothbrush according to claim 1, wherein said cam section has a plurality of cams, said cams lying in planes wherein adjacent cam planes are separated by at least 100°.

4. A toothbrush according to claim 1 further comprising a disengageable mechanical coupling between a first end of said cam shaft and an electric motor drive shaft of said motor.

5. A power driven mechanical toothbrush comprising:

an elongate shank;

a toothbrush head member attached to said shank, said head supporting a plurality of tuft blocks, said blocks having bristle tufts therein, said tufts having upstanding remote ends;

a cam shaft rotatably driven at speeds in the range of 5500 rpm to 7500 rpm within said shank, said shaft having a central longitudinal axis, said shaft formed by a wire extending directly from a motor to said head member, said shaft having a cam section that fits inside said head member;

a bearing at each end of said cam section of said shaft to minimize deflection of said cam section from said central longitudinal axis;

said tuft blocks pivotally supported by said head member about an axis parallel to and spaced apart from said central longitudinal axis, said tuft blocks having respective slots that fit loosely over said cam section such that when said cam shaft is rotated said upstanding remote ends of said bristle tufts in said tuft blocks move from side to side with respect to said shank; at least one of said tuft blocks held stationary in said head member.

6. A toothbrush according to claim 5 further comprising a bearing insert engaged in one of said slots of one of said blocks, said insert supporting and restricting deflection of said cam section.

* * * * *